United States Patent [19]

Elbe et al.

[11] Patent Number: 5,244,893
[45] Date of Patent: Sep. 14, 1993

[54] BENZOTHIOPHENE-2-CARBOXAMIDE S,S-DIOXIDES AND USE

[75] Inventors: Hans-Ludwig Elbe; Dieter Berg, both of Wuppertal; Heinz-Wilhelm Dehne, Monheim; Stefan Dutzmann, Hilden; Georg-Wilhelm Ludwig, Krefeld; Manfred Plempel, Haan, all of Fed. Rep. of Germany

[73] Assignee: Bayer Aktiengesellschaft, Leverkusen, Fed. Rep. of Germany

[21] Appl. No.: 875,868

[22] Filed: Apr. 29, 1992

[30] Foreign Application Priority Data

May 9, 1991 [DE] Fed. Rep. of Germany ....... 4115184

[51] Int. Cl.$^5$ .................... A61K 31/38; C07D 333/70
[52] U.S. Cl. ................. 514/212; 514/228.2; 514/233.5; 514/253; 514/324; 514/378; 514/422; 514/443; 504/219; 504/221; 504/225; 504/235; 504/249; 504/271; 504/287; 504/289; 540/596; 544/58.4; 544/145; 544/146; 544/376; 546/202; 548/240; 548/525; 549/53; 549/55; 549/57
[58] Field of Search ............................ 549/53, 55, 57; 514/443, 324, 422, 233.5, 212, 228.2, 253, 378; 71/90; 546/202; 548/525, 240; 544/145, 58.4, 146, 376; 540/596

[56] References Cited

U.S. PATENT DOCUMENTS 4,663,347 5/1987 Atkinson et al. .................. 548/251
5,118,680 6/1992 Müller et al. ...................... 514/324

FOREIGN PATENT DOCUMENTS 0146243 10/1984 European Pat. Off. .
160408 11/1985 European Pat. Off. ............. 549/53
3832846 9/1988 Fed. Rep. of Germany .
3832848 3/1990 Fed. Rep. of Germany ........ 549/53
2193961 8/1987 United Kingdom .

OTHER PUBLICATIONS

Erble (II), Derwent Abstract of DE 3832846 (1990).
Elbe, et al Chemical Abstracts, vol. 113, 1990, p. 340.

Primary Examiner—Richard L. Raymond
Attorney, Agent, or Firm—Sprung Horn Kramer & Woods

[57] ABSTRACT

New compounds of the formula (I)

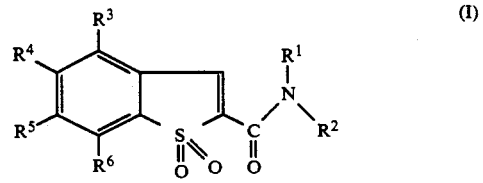

in which $R^1$–$R^6$ have the meanings given in the description, their preparation and use in plant protection, the protection of materials and in the field of human and veterinary medicine.

Formula (I) gives a definition of the compounds which can be prepared by analogous processes, for example from suitable benzothiophene derivatives by oxidation.

6 Claims, No Drawings

BENZOTHIOPHENE-2-CARBOXAMIDE S,S-DIOXIDES AND USE

The invention relates to new benzothiophene-2-carboxamide S,S-dioxides, to a process for their preparation, and to their use for combating pests in a variety of fields, for example in plant protection, the protection of materials, and in the field of human and veterinary medicine.

It has been disclosed that certain benzothiophene-2-carboxamide S,S-dioxides such as, for example, the compound 3-chloro-N-(1-phenylethyl)-benzothiophene-2-carboxamide S,S-dioxide, have fungicidal properties (compare, for example, DE-OS (German Published Specification) 3,832,848).

However, the activity of these previously known compounds is not entirely satisfactory in all fields of application, in particular when the application rates and concentrations are low.

Furthermore, it is known that certain benzothiophene-2-carboxamide S,S-dioxides such as, for example, the compound 3-(1-imidazolyl)-N-(1-phenylethyl)-benzothiophene-2-carboxamide S,S-dioxide or the compound 3-methylthio-N-(1-phenylethyl)-benzothiophene-2-carboxamide S,S-dioxide, have a good antimycotic activity (compare, for example, DE-OS (German Published Specification) 3,832,848).

However, the activity of these previously known compounds is not entirely satisfactory in all indications.

There are also known certain benzothiophene-2-carboxamide derivatives (compare, for example, EP 146,243 or GB 2,193,961), whose activity is presently still unknown.

There have been found new benzothiophene-2-carboxamide S,S-dioxides of the general formula (I)

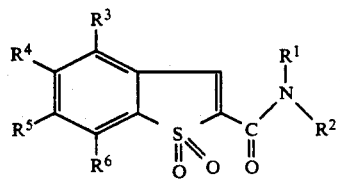

in which $R^1$ represents optionally substituted alkyl, or represents alkenyl or alkynyl, or represents in each case optionally substituted cycloalkyl or cycloalkylalkyl, or represents in each case optionally substituted aralkyl, aralkenyl, aralkynyl or aryl, $R^2$ represents hydrogen or optionally substituted alkyl or $R^1$ and $R^2$ together with the nitrogen atom to which they are bonded represent an optionally substituted heterocycle and $R^3$, $R^4$, $R^5$ and $R^6$ independently of one another in each case represent hydrogen, halogen, cyano, nitro, alkyl, alkoxy, alkylthio, halogenoalkyl, halogenoalkoxy or halogenoalkylthio.

Furthermore, it has been found that the new benzothiophene-2-carboxamide S,S-dioxides of the general formula (I)

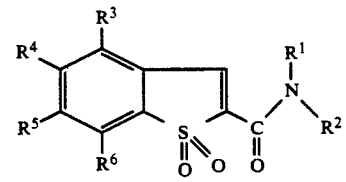

in which $R^1$ represents optionally substituted alkyl, or represents alkenyl or alkynyl, or represents in each case optionally substituted cycloalkyl or cycloalkylalkyl, or represents in each case optionally substituted aralkyl, aralkenyl, aralkynyl or aryl, $R^2$ represents hydrogen or optionally substituted alkyl or $R^1$ and $R^2$ together with the nitrogen atom to which they are bonded represent an optionally substituted heterocycle and $R^3$, $R^4$, $R^5$ and $R^6$ independently of one another in each case represent hydrogen, halogen, cyano, nitro, alkyl, alkoxy, alkylthio, halogenoalkyl, halogenoalkoxy or halogenoalkylthio, are obtained when benzothiophene-2-carboxamides of the general formula (II)

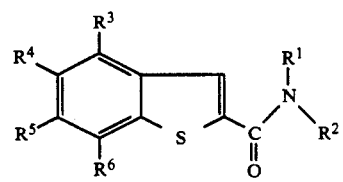

in which $R^1$, $R^2$, $R^3$, $R^4$, $R^5$ and $R^6$ have the abovementioned meaning, are reacted with an oxidant, if appropriate in the presence of a diluent and, if appropriate, in the presence of a reaction auxiliary.

Finally, it has been found that the new benzothiophene2-carboxamide S,S-dioxides of the general formula (I) have a good activity against pests in a wide range of fields, for example against fungi in plant protection, against microorganisms in the protection of materials and, for example, in the field of human medicine.

Surprisingly, the benzothiophene-2-carboxamide S,S-dioxides of the general formula (I) exhibit a better fungicidal activity than the benzothiophene-2-carboxamide S,S-dioxides known from the prior art, such as, for example, the compound 3-chloro-N-(1-phenylethyl)-benzothiophene-2-carboxamide S,S-dioxide, which are similar compounds chemically and from the point of the view of their action. Moreover, they exhibit a clearly better antimycotic activity than the benzothiophene-2-carboxamide S,S-dioxides known from the prior art such as, for example, the compound 3-(1-imidazolyl)-N-(1-phenylethyl)benzothiophene-2-carboxamide S,S-dioxide or the compound 3-methylthio-N-(1-phenylethyl)-benzothiophene-2-carboxamide S,S-dioxide, which are similar compounds chemically and from the point of view of their action.

Formula (I) provides a general definition of the benzothiophene-2-carboxamide S,S-dioxides according to the invention. Preferred compounds of the formula (I) are those in which $R^1$ represents straight-chain or branched alkyl having 1 to 20 carbon atoms, or represents in each case straight-chain or branched halogenoalkyl, cyanoalkyl, hydroxyalkyl, alkoxyalkyl or alkoxycarbonylalkyl, each of which has 1 to 8 carbon atoms in the individual alkyl moieties, or represents straight-chain or branched alkenyl having 2 to 12 carbon atoms, or represents straight-chain or branched alkynyl having 2 to 12 carbon atoms, or represents cycloalkylalkyl or cycloalkyl, each of which has 3 to 7 carbon atoms in the cycloalkyl moiety and, if appropriate, 1 to 6 carbon atoms in the straight-chain or branched alkyl moiety, and each of which is optionally monosubstituted to hexasubstituted in the cycloalkyl moiety by identical or different substituents, suitable cycloalkyl substituents in each case being: halogen, in each case straight-chain or branched alkyl having 1 to 4 carbon atoms or in each case straight-chain or branched halogenoalkyl having 1 to 4 carbon atoms and 1 to 9 identical or different halogen atoms; furthermore represents arylalkyl, arylalkenyl, arylalkynyl or aryl, each of which has 6 or 10 carbon atoms in the aryl moiety and, if appropriate, up to 12 carbon atoms in the respective straight-chain or branched alkyl or alkenyl or alkynyl moiety, each of which is optionally monosubstituted to pentasubstituted in the aryl moiety by identical or different substituents, suitable aryl substituents in each case being: halogen, cyano, nitro, formylamido, in each case straight-chain or branched alkyl, alkoxy or alkylthio, each of which has 1 to 4 carbon atoms, in each case straight-chain or branched halogenoalkyl, halogenoalkoxy, halogenoalkylthio, each of which has 1 to 4 carbon atoms and 1 to 9 identical or different halogen atoms, in each case straight-chain or branched alkylcarbonyl, alkoxycarbonyl, aminocarbonyl, N-alkylaminocarbonyl, N,N-dialkylaminocarbonyl, alkylcarbonylamino, N-alkyl-alkylcarbonylamino, N-alkyl-formylcarbonylamino or alkoximinoalkyl, each of which has 1 to 4 carbon atoms in the individual alkyl moieties, and phenyl which is optionally monosubstituted or polysubstituted by identical or different substituents from the series comprising halogen and/or straight-chain or branched alkyl having 1 to 4 carbon atoms, $R^2$ represents hydrogen or straight-chain or branched alkyl which has 1 to 6 carbon atoms and which is optionally monosubstituted or polysubstituted by identical or different substituents, suitable substituents being: hydroxyl, halogen, cyano, and in each case straight-chain or branched alkoxy, alkoxycarbonyl or dialkylamino, each of which has 1 to 6 carbon atoms in the individual alkyl moieties, or $R^1$ and $R^2$ together with the nitrogen atom to which they are bonded represent a saturated 5- to 7-membered heterocycle which is optionally monosubstituted or polysubstituted by identical or different substituents and which can optionally contain 1 or 2 further hetero atoms, in particular nitrogen, oxygen and/or sulphur, suitable substituents in each case being: halogen, in each case straight-chain or branched alkyl, alkoxy or alkoxy carbonyl having in each case 1 to 4 carbon atoms or straight-chain or branched halogenoalkyl having 1 to 4 carbon atoms and 1 to 9 identical or different halogen atoms and $R^3$, $R^4$, $R^5$ and $R^6$ independently of one another in each case represent hydrogen, halogen, cyano, nitro or in each case straight-chain or branched alkyl, alkoxy, alkylthio, halogenoalkyl, halogenoalkoxy or halogenoalkylthio each of which has 1 to 6 carbon atoms and if appropriate 1 to 13 identical or different halogen atoms.

Particularly preferred compounds of the formula (I) are those in which $R^1$ represents straight-chain or branched alkyl having 1 to 18 carbon atoms, in each case straight-chain or branched halogenoalkyl, cyanoalkyl, hydroxyalkyl, alkoxyalkyl or alkoxycarbonylalkyl, each of which has 1 to 4 carbon atoms in the individual alkyl moieties, or represents straight-chain or branched alkenyl having 2 to 8 carbon atoms, or represents straight-chain or branched alkynyl having 2 to 8 carbon atoms, or represents cycloalkylalkyl or cycloalkyl, each of which has 3 to 6 carbon atoms in the cycloalkyl moiety and, if appropriate, 1 to 4 carbon atoms in the straight-chain or branched alkyl moiety and each of which is optionally monosubstituted to tetrasubstituted in the cycloalkyl moiety by identical or different substituents, suitable cycloalkyl substituents in each case being: fluorine, chlorine, bromine, methyl, ethyl, n- or i-propyl, n-, i-, s- or t-butyl, chloromethyl, dichloromethyl or trifluoromethyl; moreover arylalkyl, arylalkenyl, arylalkynyl or aryl, each of which has 6 or 10 carbon atoms in the aryl moiety and, if appropriate, up to 8 carbon atoms in the particular straight-chain or branched alkyl or alkenyl or alkynyl moiety and each of which is optionally monosubstituted to pentasubstituted in the aryl moiety by identical or different substituents, suitable aryl substituents in each case being: halogen, hydroxyl, cyano, nitro, formylamido, in each case straight-chain or branched alkyl, alkoxy or alkylthio, each of which has 1 to 4 carbon atoms, in each case straight-chain or branched halogenoalkyl, halogenoalkoxy, halogenoalkylthio, each of which has 1 to 4 carbon atoms and 1 to 9 identical or different halogen atoms, in each case straight-chain or branched alkylcarbonyl, alkoxycarbonyl, aminocarbonyl, N-alkylaminocarbonyl, N,N-dialkylaminocarbonyl, alkylcarbonylamino, N-alkyl-alkylcarbonylamino, N-alkyl-formylcarbonylamino or alkoximinoalkyl, each of which has 1 to 4 carbon atoms in the individual alkyl moieties, and phenyl which is optionally monosubstituted or polysubstituted by identical or different substituents from the series comprising halogen and/or straight-chain or branched alkyl having 1 to 4 carbon atoms, $R^2$ represents hydrogen or alkyl which has 1 to 4 carbon atoms and which is optionally monosubstituted or polysubstituted by identical or different substituents, suitable substituents being: hydroxyl, halogen, cyano and in each case straight-chain or branched alkoxy, alkoxycarbonyl or dialkylamino, each of which has 1 to 4 carbon atoms in the individual alkyl moieties, or $R^1$ and $R^2$ together with the nitrogen atom to which they are bonded represent a heterocycle of the formula

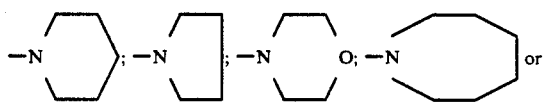

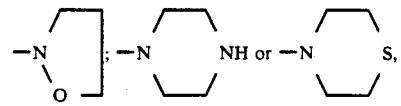

each of which is optionally monosubstituted to tetrasubstituted by identical or different substituents, suitable substituents in each case being: fluorine, chlorine, bromine, methyl, ethyl, n- or i-propyl, methoxy, ethoxy, methoxycarbonyl, ethoxycarbonyl, chloromethyl, trichloromethyl, dichloromethyl or trifluoromethyl, and $R^3$, $R^4$, $R^5$ and $R^6$ independently of one another in each case represent hydrogen, halogen, cyano, nitro or in each case straight-chain or branched alkyl, alkoxy, alkylthio, halogenoalkyl, halogenoalkoxy or halogenoalkylthio, each of which has 1 to 4 carbon atoms and, if appropriate, 1 to 9 identical or different halogen atoms.

Very particularly preferred compounds of the formula (I) are those in which $R^1$ represents methyl, ethyl, n- or i-propyl, n-, i-, s-or t-butyl, n- or i-pentyl, n- or i-hexyl, n- or i-heptyl, n- or i-octyl, n- or i-nonyl, n- or i-decyl, n- or i-dodecyl, n- or i-octadecyl, allyl, n- or i-butenyl, n- or i-pentenyl, n- or i-hexenyl, propargyl, n- or i-butinyl, n- or i-pentinyl, n- or i-hexinyl, chloromethyl, bromomethyl, chloroethyl, bromoethyl, chloropropyl, bromopropyl, cyanomethyl, cyanoethyl, cyanopropyl, hydroxymethyl, hydroxyethyl, hydroxypropyl, methoxymethyl, methoxyethyl, methoxypropyl, ethoxymethyl, ethoxyethyl, ethoxypropyl, methoxycarbonylmethyl,methoxycarbonylethyl, methoxycarbonylpropyl,ethoxycarbonylmethyl,ethoxycarbonylethyl, ethoxycarbonylpropyl, propoxycarbonylmethyl, propoxycarbonylethyl, propoxycarbonylpropyl; furthermore represents cyclopropyl, cyclopropylmethyl, cyclopropylethyl, cyclopropylpropyl, cyclopentyl, cyclopentylmethyl, cyclopentylethyl, cyclopentylpropyl, cyclohexyl, cyclohexylmethyl, cyclohexylethyl or cyclohexylpropyl, each of which is optionally monosubstituted to tetrasubstituted in the cycloalkyl moiety by identical or different substituents from the series comprising fluorine, chlorine, bromine, methyl, ethyl, n- or i-propyl, chloromethyl, dichloromethyl or trifluoromethyl; furthermore represents phenylalkyl, phenylalkenyl, phenylalkynyl, phenyl or naphthyl, each of which has, if appropriate, up to 6 carbon atoms in the straight-chain or branched alkyl or alkenyl or alkinyl moiety and each of which is optionally monosubstituted to trisubstituted in the aryl moiety by identical or different substituents, suitable aryl substituents in each case being: fluorine, chlorine, bromine, hydroxyl, cyano, nitro, methyl, ethyl, n- or i-propyl, n-, i-, s- or t-butyl, methoxy, ethoxy, n- or i-propoxy, n-, i-, s- or t-butoxy, methylthio, ethylthio, trifluoromethyl, trifluoromethoxy, trifluoromethylthio, methylcarbonyl, ethylcarbonyl, methoxycarbonyl, ethoxycarbonyl, aminocarbonyl, N-methylaminocarbonyl, N,N-dimethylaminocarbonyl, N-ethylaminocarbonyl, N,N-diethylaminocarbonyl, N-formylamino, N-acetylamino, N-methyl-N-formylamino, N-methylN-acetylamino, N-ethyl-N-formylamino, N-ethylN-acetylamino, methoximinomethyl, methoximinoethyl, ethoximinomethyl, ethoximinoethyl, or phenyl which is optionally monosubstituted to trisubstituted by identical or different substituents from the series comprising fluorine, chlorine, bromine, methyl and/or ethyl, $R^2$ represents hydrogen, methyl, ethyl, n- or i-propyl, n-, i-, s- or t-butyl, n- or i-pentyl, n- or i-hexyl, hydroxymethyl, hydroxyethyl, hydroxypropyl, chloromethyl, bromomethyl, chloroethyl, bromoethyl, chloropropyl, bromopropyl, cyanomethyl, cyanoethyl, cyanopropyl, hydroxymethyl, hydroxyethyl, hydroxypropyl, methoxymethyl, methoxyethyl, methoxypropyl, ethoxymethyl, ethoxyethyl, ethoxypr-opyl, methoxycarbonylmethyl, methoxycarbonylethyl, methoxycarbonylpropyl, ethoxycarbonylmethyl, ethoxycarbonylethyl, ethoxycarbonylpropyl, propoxycarbonylmethyl, propoxycarbonylethyl, propoxycarbonylpropyl, dimethylaminomethyl, diethylaminomethyl, dipropylaminomethyl, dimethylaminoethyl, diethylaminoethyl, dipropylaminoethyl, dimethylaminopropyl, diethylaminopropyl or dipropylaminopropyl or $R^1$ and $R^2$ together with the nitrogen atom to which they are bonded represent a heterocycle of the formula

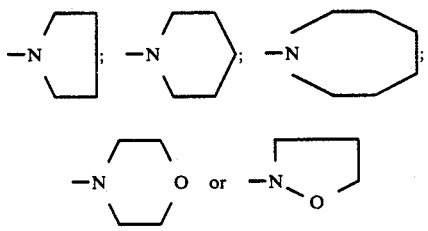

each of which is optionally monosubstituted, disubstituted or trisubstituted by methyl and/or ethyl and/or methoxycarbonyl, ethoxycarbonyl;

$R^3$, $R^4$, $R^5$ and $R^6$ independently of one another in each case represent hydrogen, fluorine, chlorine, bromine, cyano, nitro, methyl, ethyl, n- or i-propyl, n-, i-, s- or t-butyl, methoxy, ethoxy n- or i-propoxy, n-, i-, s- or t-butoxy, methylthio, ethylthio, trifluoromethyl, methyl, trifluoromethoxy or trifluoromethylthio.

Compounds which may be mentioned individually are those given in the Preparation Examples.

If, for example, benzothiophene-2-carboxanilide is used as starting compound and hydrogen peroxide as oxidant, the course of the reaction of the process according to the invention can be represented by the following equation:

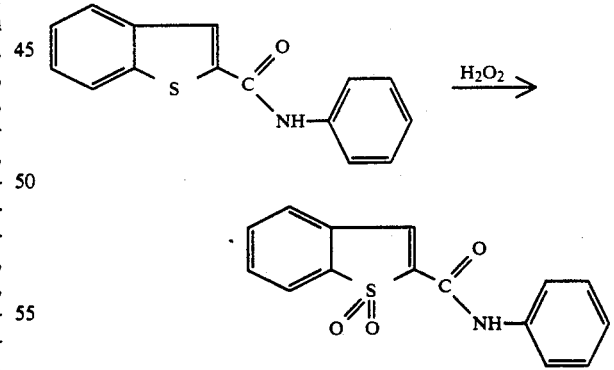

Formula (II) provides a general definition of the benzothiophene-2-carboxamides required as starting substances for carrying out the process according to the invention. In this formula (II), $R^1$, $R^2$, $R^3$, $R^4$, $R^5$ and $R^6$ preferably represent those radicals which have already been mentioned in connection with the description of the compound of the formula (I) according to the invention as being preferred for these substituents.

The benzothiophene-2-carboxamides of the formula (II) are known or can be obtained in analogy to the known processes (compare, for example, EP 374,048; EP 253,650; Ind J. Chem. Sect. B, 23B, 38-41 [1984]; Tetrahedron 34, 3545-3551 [1978]; Collect. Czech. Chem. Commun. 51, 2002-2012 [1986]; J. org. Chem. 40, 3037-3045 [1975]; Liebigs Ann. Chem. 760, 37-87 [1972] and the Preparation Examples).

Suitable oxidants for carrying out the process according to the invention are all oxidants which can customarily be used for sulphur oxidations. The following are preferably used: hydrogen peroxide or organic peracids such as, for example, peracetic acid, 4-nitroperbenzoic acid or 3-chloroperbenzoic acid, or inorganic oxidants such as periodic acid, potassium permanganate or chromic acid.

Diluents for carrying out the process according to the invention are inorganic or organic solvents, depending on the oxidant used. The following are preferably used: alcohols such as, for example, methanol or ethanol, or their mixtures with water, or pure water; acids such as, for example, acetic acid, acetic anhydride or propionic acid, or dipolar aprotic solvents such as acetonitrile, acetone, ethyl acetate or dimethylformamide, and also optionally halogenated hydrocarbons such as benzine, benzene, toluene, hexane, cyclohexane, petroleum ether, dichloromethane, dichloroethane, chloroform, carbon tetrachloride or chlorobenzene.

If appropriate, the process according to the invention can be carried out in the presence of a reaction auxiliary. Suitable reaction auxiliaries are all organic or inorganic acid-binding agents which can customarily be used. The following are preferably used: the hydroxides, acetates or carbonates of alkaline earth metals or alkali metals such as, for example, calcium hydroxide, sodium hydroxide, sodium acetate or sodium carbonate.

If appropriate, the process according to the invention can also be carried out in the presence of a suitable catalyst. Catalysts which are suitable are all catalysts which can customarily be used for such sulphur oxidations. Heavy-metal catalysts are preferably used; ammonium molybdate may be mentioned in this context by way of example.

When carrying out the process according to the invention, the reaction temperatures can be varied within a substantial range. In general, the process is carried out at temperatures between $-30°$ C. and $+100°$ C., preferably at temperatures between $0°$ C. and $+80°$ C.

For carrying out the process according to the invention, 2.0 to 10.0 moles, preferably 2.0 to 5.0 moles, of oxidant, if appropriate 1.0 to 1.5 moles, preferably 1.0 to 1.3 moles, of base used as reaction auxiliary and, if appropriate, 0.001 to 1.0 mole, preferably 0.005 to 0.05 mole, of catalyst are generally employed per mole of benzothiophene-2-carboxamide of the formula (II). The reaction is carried out and the reaction products are worked up and isolated by known processes (compare, in this context, the Preparation Examples).

The active compounds according to the invention have a powerful action against pests and can be employed in practice for combating undesirable harmful organisms. The active substances are suitable, inter alia, for use as plant protection agents, in particular as fungicides.

Fungicidal agents in plant protection are employed for combating Plasmodiophoromycetes, Oomycetes, Chytridiomycetes, Zygomycetes, Ascomycetes, Basidiomycetes and Deuteromycetes.

Some causative organisms of fungal diseases which come under the generic names listed above may be mentioned as examples, but not by way of limitation:

Pythium species, such as, for example, *Pythium ultimum;* Phytophthora species, such as, for example, *Phytophthora infestans;*

Pseudoperonospora species, such as, for example, *Pseudoperonospora humuli* or *Pseudoperonospora cubensis;*

Plasmopara species, such as, for example, *Plasmopara viticola;*

Peronospora species, such as, for example, *Peronospora pisi* or *P. brassicae;*

Erysiphe species, such as, for example, *Erysiphe graminis;*

Sphaerotheca species, such as, for example, *Sphaerotheca fuliginea;*

Podosphaera species, such as, for example, *Podosphaera leucotricha;*

Venturia species, such as, for example, *Venturia inaequalis;*

Pyrenophora species, such as, for example, *Pyrenophora teres* or *P. graminea* (conidia form: Drechslera, syn: Helminthosporium);

Cochliobolus species, such as, for example, *Cochliobolus sativus* (conidia form: Drechslera, syn: Helminthosporium);

Uromyces species, such as, for example, *Uromyces appendiculatus;*

Puccinia species, such as, for example, *Puccinia recondita;*

Tilletia species, such as, for example, *Tilletia caries;*

Ustilago species, such as, for example, *Ustilago nuda* or Ustilago avenae;

Pellicularia species, such as, for example, *Pellicularia sasakii;*

Pyricularia species, such as, for example, *Pyricularia oryzae;*

Fusarium species, such as, for example, *Fusarium culmorum;*

Botrytis species, such as, for example, *Botrytis cinerea;* Septoria species, such as, for example, *Septoria nodorum;* Leptosphaeria species, such as, for example, *Leptosphaeria nodorum;*

Cercospora species, such as, for example, *Cercospora canescens;*

Alternaria species, such as, for example, *Alternaria brassicae;*

Pseudocercosporella species, such as, for example, *Pseudocercosporella herpotrichoides.*

The good toleration, by plants, of the active compounds, at the concentrations required for combating plant diseases, permits treatment of above-ground parts of plants, of vegetative propagation stock and seeds, and of the soil.

In this context, the active compounds according to the invention can be employed with particularly good success for combating cereal diseases such as, for example, against the causative organism of powdery mildew of cereals (*Erysiphe graminis*) or against the causative organism of net blotch of barley (*Pyrenophora teres*) or against the causative organism of foot rot of barley or wheat (*Cochliobolus sativus*) or against the causative organism of leaf spot of wheat (*Leptosphaeria nodorum*) or for combating diseases in fruit and vegetable growing such as, for example, against the causative organism of apple scab (*Venturia inaequalis*) or against Oomycetes or for combating rice diseases such as, for example, the causative organism of rice blast disease (*Pyricularia oryzae*) or against the causative organism of rice stem blight (*Pellicularia sasakii*). Besides, the active compounds according to the invention have a broad invitro activity.

Besides the abovementioned activity against cytopathogenic microorganisms, the active compounds according to the invention are distinguished by a powerful microbicidal action against the broad range of microorganisms which are relevant for the protection of materials.

Insofar, the substances according to the invention are outstandingly suitable for the protection of industrial materials.

Industrial materials in this context are non-live materials which have been prepared for use in industry. For example, industrial materials which are to be protected by active compounds according to the invention from microbial change or destruction can be glues, sizes, paper and board, textiles, leather, wood, paints and plastic articles, cooling lubricants and other materials which can be attacked or decomposed by microorganisms. Parts of production plants, for example cooling-water circuits, which may be impaired by the multiplication of microorganisms may also be mentioned within the scope of the materials to be protected. Industrial materials which may be mentioned within the scope of the present invention are preferably glues, sizes, papers and boards, leather, wood, paints, plastic articles, cooling lubricants and cooling circuits. Microorganisms, capable of degradation or change of the industrial materials, which may be mentioned are, for example, bacteria, fungi, yeasts, algae and slime organisms. The active compounds according to the invention preferably act against fungi, in particular moulds, wood-discolouring and wood-destroying fungi (Basidiomycetes), and against slime organisms and algae.

Microorganisms of the following genera may be mentioned as examples:
Alternaria, such as *Alternaria tenuis*,
Aspergillus, such as *Aspergillus niger*,
Chaetomium, such as *Chaetomium globosum*,
Coniophora, such as *Coniophora puteana*,
Lentinus, such as *Lentinus tigrinus*,
Penicillium, such as *Penicillium glaucum*,
Polyporus, such as *Polyporus versicolor*,
Aureobasidium, such as *Aureobasidium pullulans*,
Sclerophoma, such as *Sclerophoma pityophila*,
Trichoderma, such as *Trichoderma viride*,
Escherichia, such as *Escherichia coli*,
Pseudomonas, such as *Pseudomonas aeruginosa*,
Staphylococcus, such as *Staphylococcus aureus*.

Depending on their particular physical and/or chemical properties, the active compounds can be converted to the customary formulations which suit the field of application in question, such as solutions, emulsions, suspensions, powders, foams, pastes, granules, aerosols, very fine capsules in polymeric substances and in coating compositions for seed, as well as ULV cold mist and warm mist formulations.

These formulations are produced in a known manner, for example by mixing the active compounds with extenders, that is, liquid solvents, liquefied gases under pressure, and/or solid carriers, optionally with the use of surface-active agents, that is, emulsifying agents and/or dispersing agents and/or foam-forming agents. In the case of the use of water as an extender, organic solvents such as, for example, alcohols, might, for example, also be used as auxiliary solvents. As liquid solvents, there are suitable in the main: aromatics, such as xylene, toluene or alkylnaphthalenes, chlorinated aromatics or chlorinated aliphatic hydrocarbons, such as chlorobenzenes, chloroethylenes such as 1,2-dichloroethane or methylene chloride, aliphatic hydrocarbons, such as cyclohexane or paraffins, for example benzine and other mineral oil fractions, alcohols, such as ethanol, isopropanol, butanol, benzyl alcohol or glycol as well as their ethers and esters, ketones, such as acetone, methyl ethyl ketone, methyl isobutyl ketone or cyclohexanone, strongly polar solvents, such as dimethylformamide and dimethyl sulphoxide, as well as water; by liquefied gaseous extenders or carriers are meant liquids which are gaseous at ambient temperature and under atmospheric pressure, for example aerosol propellants, such as halogenohydrocarbons as well as butane, propane, nitrogen and carbon dioxide; as solid carriers there are suitable: for example ground natural minerals, such as kaolins, clays, talc, chalk, quartz, attapulgite, montmorillonite or diatomaceous earth, and ground synthetic minerals, such as highly-disperse silica, alumina and silicates; as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, maize cobs and tobacco stalks; as emulsifying and/or foam-forming agents there are suitable: for example non-ionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates as well as albumen hydrolysis products; as dispersing agents there are suitable: for example lignin-sulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Other additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 per cent by weight of active compound, preferably between 0.5 and 90%.

The active compounds according to the invention can be present in the formulation as a mixture with other active compounds such as fungicides, insecticides, acaricides and herbicides, and in mixtures with fertilisers and growth regulators.

The active compounds can be applied as such, in the form of their formulations or in the use forms prepared from these formulations, such as ready-for-use solutions, suspensions, wettable powders, pastes, soluble powders, dusting agents and granules. They are applied in the customary manner, for example by pouring, spraying, atomising, scattering, dusting, foaming, brushing on and the like. It is furthermore possible to apply the active compounds by the ultra-low-volume method or to inject the active compound preparation or the active compound itself into the soil. The seed of the plant can also be treated.

In the treatment of parts of plants, the active compound concentrations in the use forms can be varied within a substantial range. They are generally between 1 and 0.0001% by weight, preferably between 0.5 and 0.001% by weight.

In the treatment of seed, amounts of active compound of 0.001 to 50 g per kilogram seed, preferably 0.01 to 10 g, are generally required.

In the treatment of the soil, active compound concentrations of 0.00001 to 0.1% by weight, preferably 0.0001 to 0.02% by weight, are required at the site of action.

Microbicidalagents generally contain the active compounds in an amount of 1 to 95%, preferably 10 to 75%.

The use concentrations of the active compounds according to the invention depend on the species and the occurrence of the microorganisms to be combated, and on the composition of the material to be protected. The optimum amount to be used can be determined by test series. In general, the use concentrations are in the range from 0.001 to 5% by weight, preferably 0.05 to 1.0% by weight, relative to the material to be protected.

When used as agents for the protection of material, the active compounds according to the invention can also exist as a mixture with other known active compounds. The following active compounds may be mentioned by way of example: benzyl alcohol mono (or -poly)hemiformal and other formaldehyde-releasing compounds, benzimidazolylmethyl carbamates, tetramethyldiuram disulphide, zinc salts of dialkyl dithiocarbamates, 2,4,5,6-tetrachloroisophthalonitrile, thiazolylbenzimidazole, mercaptobenzothiazole, organotin compounds, methylenebisthiocyanate, phenol derivatives such as 2-phenylphenol, (2,2,-dihydroxy-5,5,-dichloro)-diphenylmethane, 3-methyl-4-chlorophenol and 2-thiocyanatomethylthiobenzothiazole, N-trihalogenomethylthio compounds such as folpet, fluorofolpet and dichlofluanid, azole fungicides such as triadimefon, triadimenol, bitertanol, tebuconazole, propiconazole, azaconazole, iodopropargyl derivatives such as, for example, iodopropargylbutyl carbamate (IPBC) and iodopropargylphenyl carbamate, isothiazolinone compounds such as kathon as well as quaternary ammonium compounds such as benzalkonium chloride. Mixtures of the substances to be used according to the invention with known insecticides can also be used. The following may be mentioned by way of example: organophosphorus compounds such as chloropyriphos or phoxim, carbamates such as aldicarb, carbosulphan or propoxur, or pyrethroids such as permethrin, cyfluthrin, cypermethrin, deltamethrin or fenvalerate.

Other suitable components in the mixture are algicides, molluscicides and active compounds against "sea animals" which colonise ships' bottom paints.

In addition, the compounds of the formula (I) according to the invention also exhibit good antimicrobial, in particular good antimycotic, actions. They have a very broad antimycotic spectrum of action, in particular against dermatophytes and yeasts as well as biphasic fungi, for example against Candida species such as *Candida albicans*, Epidermophyton species, such as *Epidermophyten floccossum*, Aspergillus species, such as *Aspergillus niger* and *Aspergillus fumigatus*, Trichophyton species, such as *Trichophyton mentagrophytes*, Microsporon species, such as *Microsporon felineum*, and against Torulopsis species such as *Torulopsis glabrata*. The enumeration of these microorganisms in no case represents a restriction of the microorganisms which can be combated, but has illustrating character only.

The following may be mentioned as examples for indications in human medicine: dermatomycoses and systemic mycoses caused by *Trichophyton mentagrophytes* and other Trichophyton species, Microsporon species as well as *Epidermophyton floccosum*, yeasts and biphasic fungi as well as moulds.

The following may be mentioned as examples of indications in veterinary medicine: all dermatomycoses and systemic mycoses, in particular those caused by the abovementioned causative organisms.

The present invention includes pharmaceutic preparations which contain, in addition to non-toxic, inert, pharmaceutically suitable excipients, one or more active compounds which can be used according to the invention or which consist of one or more active substances which can be used according to the invention.

The present invention also includes pharmaceutic preparations in dosage units. This means that the preparations exist in the form of individual units, for example tablets, coated tablets, capsules, pills, suppositories and ampoules, whose active compound content corresponds to a fraction or a multiple of an individual dose. The dosage units can contain, for example, 1, 2, 3 or 4 individual doses or $\frac{1}{2}$, $\frac{1}{3}$ or $\frac{1}{4}$ of an individual dose. An individual dose preferably contains the amount of active compound which is administered during one application and which usually corresponds to a whole, a half, a third or a quarter of, a daily dose.

Non-toxic, inert pharmaceutically suitable excipients are to be understood as meaning solid, semi-solid or liquid diluents, bulking agents or formulation auxiliaries of any type.

Preferred pharmaceutical preparations which may be mentioned are tablets, coated tablets, capsules, pills, granules, suppositories, solutions, suspensions and emulsions, pastes, ointments, gels, creams, lotions, powders or sprays.

Tablets, coated tablets, capsules, pills and granules can contain the active compound, or active compounds, besides the customary excipients, such as (a) bulking agents and extenders, for example starches, lactose, sucrose, glucose, mannitol and silica, (b) binders for example carboxymethylcellulose, alginates, gelatine and polyvinylpyrrolidone, (c) humectants, for example glycerol, (d) disintegrants, for example agar-agar, calcium carbonate and sodium bicarbonate, (e) solution retardants, for example paraffin, (f) resorption accelerators, for example quaternary ammonium compounds, (g) wetting agents, for example cetyl alcohol and glycerol monostearate, (h) absorbants, for example kaolin and bentonite, (i) gliding agents, for example talc, calcium stearate and magnesium stearate, and solid polyethylene glycols, or mixtures of the substances mentioned under (a) to (i).

The tablets, coated tablets, capsules, pills and granules can be provided with the customary coatings and shells, if appropriate containing opacifying agents, and can be composed in such a manner that they release the active compound, or active compounds, only or preferentially in a certain part of the intestinal tract, if appropriate with a delay, it being possible, for example, to use polymeric substances and waxes as embedding compositions.

If appropriate, the active compound, or active compounds, can also be present with one or more of the above-mentioned excipients in microencapsulated form.

Suppositories can contain, besides the active compound, or active compounds, the customary water-soluble and water-insoluble excipients, for example polyethylene glycols and fats, for example cocoa fat and higher esters, for example $C_{14}$-alcohol with $C_{16}$-fatty acid, or mixtures of these substances.

Ointments, pastes, creams and gels can contain, besides the active compound, or active compounds, the customary excipients such as animal and vegetable fats, waxes, paraffins, starches, tragacanth, cellulose derivatives, polyethylene glycols, silicones, bentonites, silica, talc and zinc oxide, or mixtures of these substances.

Powders and sprays can contain, besides the active compound, or active compounds, the customary excipients, for example lactose, talc, silica, aluminium hydroxide, calcium silicate and polyamide powder, or mixtures of these substances, and sprays can additionally contain the customary propellants, for example chlorofluorohydrocarbons.

Solutions and emulsions can contain, beside the active compound, or active compounds, the customary excipients such as solvents, solution retardants and emulsifiers, for example water, ethyl alcohol, isopropyl alcohol, ethyl carbonate, ethyl acetate, benzyl alcohol, benzyl benzoate, propylene glycol, 1,3-butylene glycol, dimethylformamide, oils, in particular cotton seed oil, groundnut oil, maize germ oil, olive oil, castor oil and sesame seed oil, glycerol, glycerol formal, tetrahydrofurfuryl alcohol, polyethylene glycol and fatty acid ester of sorbitan, or mixtures of these substances.

For parenteral administration, the solutions and emulsions can also exist in sterile and blood-isotonic form.

Suspensions can contain, besides the active compound, or active compounds, the customary excipients such as liquid diluents, for example water, ethyl alcohol, propyl alcohol, suspending agents, for example ethoxylated isostearyl alcohols, polyoxyethylene sorbitol esters and polyoxyethylene sorbitan esters, microcrystalline cellulose, aluminium metahydroxide, bentonite, agar-agar and tragacanth, or mixtures of these substances.

The said formulation forms can also contain colorants, preservatives and odour- and flavour-improving additives, for example peppermint oil and eucalyptus oil, and sweeteners, for example saccharine.

In general, the therapeutically active compounds in the abovementioned pharmaceutical preparations should be present in a concentration of approx. 0.1 to 99.5% by weight, preferably 0.5 to 95% by weight, of the total mixture.

The abovementioned pharmaceutical preparations can furthermore contain other pharmaceutical active compounds in addition to the active compounds which can be used according to the invention.

The abovementioned pharmaceutical preparations are prepared in the customary manner by known methods, for example by mixing the active compound, or active compounds, with the excipient, or the excipients.

The present invention also includes the use of the active compounds and of their pharmaceutical preparations which contain one or more of the active compounds, in human and veterinary medicine for preventing, alleviating and/or curing the abovementioned diseases.

The active compound or the pharmaceutical preparations can be administered locally, orally, parenterally, intraperitoneally and/or rectally, preferably parenterally, in particular intravenously.

In general, it has proved advantageous in both human and veterinary medicine to administer the active compound, or active compounds, which can be used according to the invention in total amounts of approx. 1 to 200, preferably approx. 5.0 to 150 mg/kg of body weight every 24 hours, if appropriate in the form of several individual doses, to achieve the desired result.

In the case of oral administration, the active compounds which can be used according to the invention are administered in total amounts of approx. 2.5 to approx. 200, preferably approx. 5 to 150, mg/kg of body weight every 24 hours, and, in the case of parenteral administration, in total amounts of approx. 1 to 50, preferably 2.5 to 25, mg/kg of body weight every 24 hours.

However, it may be necessary to deviate from the dosages mentioned, depending on the type and the body weight of the subject to be treated, the nature and severity of the disease, the type of preparation, and the administration of the medicament, and also the period or interval in which administration takes place. Thus in some cases it may be sufficient to manage with less than the abovementioned amount of active compound, whereas in other cases the abovementioned amount of active compound must be exceeded. The optimum dosage required in each case and the type of administration of the active compounds can easily be established by any person skilled in the art on the basis of his expert knowledge.

PREPARATION EXAMPLES

Example 1

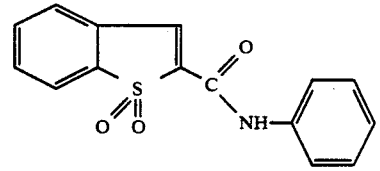

6 g (0.0237 mol) of benzothiophene-2-carboxanilide and 9.3 g (0.0947 mol) of 35 per cent strength aqueous hydrogen peroxide solution are dissolved in 47 ml of glacial acetic acid, and the mixture is stirred for 20 hours at 50° C. For working up, water is added, and precipitate which has settled out is filtered off with suction, washed twice with water and subsequently dried.

5.5 g (82% of theory) of benzothiophene-2-carboxanilide S,S-dioxide of melting point >220° C. are obtained.

Preparation of the starting compound

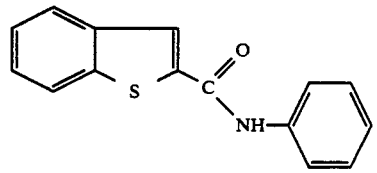

To 8 g (0.0407 mol) of benzothiophene-2-carboxylic acid chloride in 150 ml of toluene there are added with stirring at room temperature 7.6 g (0.0814 mol) of anilin, then, when the addition is complete, the mixture is stirred for 5 hours at 50° C., the reaction mixture is then poured into water, and precipitate which has settled out is filtered off with suction, washed twice with water and dried. 7.9 g (77% of theory) of benzothiophene-2-carboxanilide of melting point 188° C. are obtained.

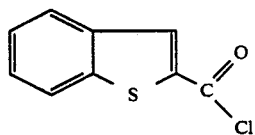

To 57.5 g (0.324 mol) of benzothiophene-2-carboxylic acid in 600 ml of chlorobenzeno there are added dropwise with stirring at reflux temperature 57.8 g (0.468 mol) of thionyl chloride and, when the addition is complete, the mixture is stirred at reflux temperature until the evolution of gas has ceased. For working up, the reaction mixture is allowed to cool to room temperature and then concentrated in vacuo, the residue is stirred with n-hexane, and precipitate which has settled out is filtered off with suction and dried.

57.4 g (90% of theory) of benzothiophene-2-carboxylic acid chloride, which can be reacted further without additional purification, are obtained.

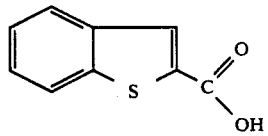

84 g (0.438 mol) of methyl benzothiophene-2-carboxylate (compare, for example, J. Org. Chem. 37. 3224 [1972]) in 218 ml of ethanol and 36.8 g (0.656 mol) of potassium hydroxide in 100 ml of water are combined, and the mixture is stirred for 4 hours at reflux temperature. For working up, the reaction mixture is allowed to cool, the ethanol is then distilled off in vacuo, the aqueous residue is washed once using diethyl ether, and subsequently acidified with dilute hydrochloric acid, and precipitate which has settled out is filtered off with suction, washed once with water and dried.

60.1 g (77% of theory) of benzothiophene-2-carboxylic acid of melting point >220° C. are obtained.

The following benzothiophene-2-carboxamide S,S-dioxides of the general formula (I)

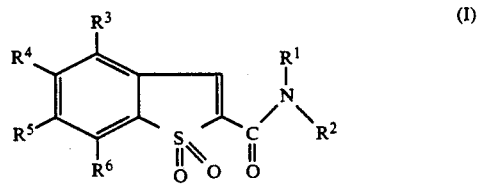

are obtained in a corresponding manner and following the general preparation instructions:

| Example No. | $R^1$ | $R^2$ | $R^3$ | $R^4$ | $R^5$ | $R^6$ | Melting point °C. |
|---|---|---|---|---|---|---|---|
| 2 | CH3-cyclohexyl (with H) | H | H | H | H | H | 183–185 |
| 3 | 2,6-dimethylphenyl | H | H | H | H | H | 125–128 |
| 4 | -CH2-(2-methylcyclohexyl) | H | H | H | H | H | 152 |
| 5 | 2-chloro-C(O)-N(CH3)-phenyl | H | H | H | H | H | >200 |
| 6 | -CH(CH3)-phenyl | H | H | H | H | H | 199 |

-continued

| Example No. | R¹ | R² | R³ | R⁴ | R⁵ | R⁶ | Melting point °C. |
|---|---|---|---|---|---|---|---|
| 7 | −CH(CH₃)−C₆H₄−Cl (4-Cl) | H | H | H | H | H | 219 |
| 8 | −CH₂−C₆H₃−Cl₂ (2,4-diCl) | H | H | H | H | H | 191 |
| 9 | −CH₂−C₆H₄−Cl (4-Cl) | H | H | H | H | H | 154 |
| 10 | −CH(CH₃)−C₆H₄−OCH₃ (4-OCH₃) | H | H | H | H | H | 134 |
| 11 | −CH₂−C₆H₄−Cl (2-Cl) | H | H | H | H | H | >230 |
| 12 | −CH(CH₃)−C₆H₃−Cl₂ (2,4-diCl) | H | H | H | H | H | 227 |
| 13 | −CH₂−C₆H₄−Br (4-Br) | H | H | H | H | H | >235 |
| 14 | −CH(CH₃)−C₆H₃−Cl₂ (3,4-diCl) | H | H | H | H | H | 165 |
| 15 | −CH₂−C₆H₅ | H | H | H | H | H | 194 |
| 16 | −CH(CH₃)−C₆H₄−OCH₃ (3-OCH₃) | H | H | H | H | H | 160 |
| 17 | −CH₂−C₆H₄−F (4-F) | H | H | H | H | H | >200 |

-continued

| Example No. | R¹ | R² | R³ | R⁴ | R⁵ | R⁶ | Melting point °C. |
|---|---|---|---|---|---|---|---|
| 18 | -CH(CH₃)-C₆H₄(2-Cl) | H | H | H | H | H | 233 |
| 19 | -CH(CH₃)-C₆H₄(4-F) | H | H | H | H | H | 235 |
| 20 | -CH(CH₃)-C₆H₄(3-Cl) | H | H | H | H | H | 211 |
| 21 | -CH(CH₃)-C₆H₄(3-CH₃) | H | H | H | H | H | 173 |
| 22 | -CH(CH₃)-C₆H₄(4-CH₃) | H | H | H | H | H | 90 |
| 23 | -CH(CH₃)-C₆H₄(2-CH₃) | H | H | H | H | H | 159 |
| 24 | -CH₂-C₆H₄(2-F) | H | H | H | H | H | 197 |
| 25 | -CH₂-C₆H₃(2,4-F₂) | H | H | H | H | H | >200 |
| 26 | -CH₂-C₆H₃(3,4-F₂) | H | H | H | H | H | >200 |
| 27 | -CH₂-C₆H₄(3-F) | H | H | H | H | H | >200 |
| 28 | -CH₂-C₆H₃(2-Cl,4-F) | H | H | H | H | H | >200 |

-continued

| Example No. | R¹ | R² | R³ | R⁴ | R⁵ | R⁶ | Melting point °C. |
|---|---|---|---|---|---|---|---|
| 29 | 4-methoxyphenyl | H | H | H | H | H | >200 |
| 30 | 4-chlorophenyl | H | H | H | H | H | >200 |
| 31 | n-C₄H₉ | H | H | H | H | H | 138 |
| 32 | phenyl | n-C₄H₉ | H | H | H | H | >200 |
| 33 | -CH₂-(4-methoxyphenyl) | H | H | H | H | H | >200 |
| 34 | CH₃ | H | H | H | H | H | >200 |
| 35 | -CH₂-(4-methylphenyl) | H | H | H | H | H | >200 |
| 36 | -CH₂-(2,4-dichlorophenyl) | CH₃ | H | H | H | H | >200 |
| 37 | cyclohexyl | H | H | H | H | H | >200 |
| 38 | -CH₂-(4-N(CH₃)₂-phenyl) | H | H | H | H | H | >200 |
| 39 | -CH₂-C(O)-O-C₂H₅ | CH₃ | H | H | H | H | Oil; ¹H-NMR*: 3,295 |
| 40 | -CH₂-C(O)-O-C₂H₅ | H | H | H | H | H | <200 |
| 41 | -CH₂-(2-chloro-4-fluorophenyl) | H | H | H | H | H | >200 |
| 42 | -CH(CH₃)-(4-methoxyphenyl) | H | H | Cl | H | H | >200 |

-continued

| Example No. | R¹ | R² | R³ | R⁴ | R⁵ | R⁶ | Melting point °C. |
|---|---|---|---|---|---|---|---|
| 43 | —CH₂—C₆H₅ (benzyl) | H | H | Cl | H | H | >200 |
| 44 | —CH₂—(2,4-dichlorophenyl) | H | H | Cl | H | H | >200 |
| 45 | —CH₂—(4-chlorophenyl) | H | H | Cl | H | H | >200 |
| 46 | —CH(CH₃)—C₆H₅ | H | H | Cl | H | H | >200 |
| 47 | 2-ethyl-6-methylphenyl | H | H | H | H | H | 152 |
| 48 | 4-chloro-2-methylphenyl | H | H | H | H | H | 206–208 |
| 49 | 3-chloro-2-methylphenyl | H | H | H | H | H | 208 |
| 50 | 2,6-dimethylphenyl | H | H | H | H | H | 174 |
| 51 | —CH₂—C₆H₅ | H | H | H | H | —O—CH₃ | >200 |
| 52 | —CH₂—(2,4-dichlorophenyl) | H | H | H | H | —O—CH₃ | >200 |
| 53 | —CH₂—(4-chlorophenyl) | H | H | H | H | —O—CH₃ | >200 |

-continued
| Example No. | R¹ | R² | R³ | R⁴ | R⁵ | R⁶ | Melting point °C. |
|---|---|---|---|---|---|---|---|
| 54 | 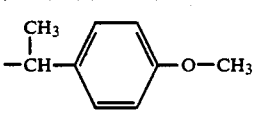 -CH(CH₃)-C₆H₄-O-CH₃ | H | H | H | H | —O—CH₃ | >200 |
| 55 | 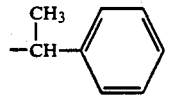 -CH(CH₃)-C₆H₅ | H | H | H | H | —O—CH₃ | >200 |
| 56 | 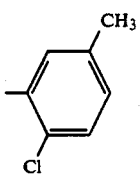 2-CH₃, 4-Cl phenyl | H | H | H | H | H | 231 |
| 57 | 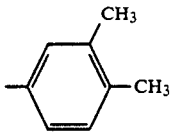 2,4-dimethylphenyl | H | H | H | H | H | >250 |
| 58 | 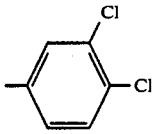 3,4-dichlorophenyl | H | H | H | H | H | >250 |
| 59 | 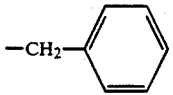 -CH₂-C₆H₅ | H | Cl | H | H | H | >200 |
| 60 | 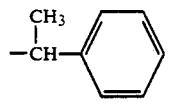 -CH(CH₃)-C₆H₅ | H | Cl | H | H | H | >200 |
| 61 | 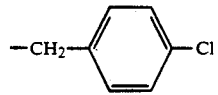 -CH₂-C₆H₄-Cl | H | Cl | H | H | H | >200 |
| 62 | 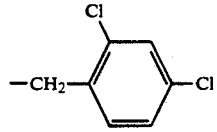 -CH₂-(2,4-diCl-C₆H₃) | H | Cl | H | H | H | >200 |
| 63 | 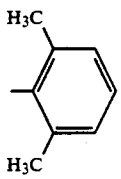 2,6-dimethylphenyl | H | H | H | H | H | 208–210 |
| 64 | 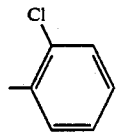 2-chlorophenyl | H | H | H | H | H | 187–189 |

-continued

| Example No. | R¹ | R² | R³ | R⁴ | R⁵ | R⁶ | Melting point °C. |
|---|---|---|---|---|---|---|---|
| 65 | 2,3-dichlorophenyl | H | H | H | H | H | 192–194 |
| 66 | 2-methylphenyl | H | H | H | H | H | 154 |
| 67 | 4-(trifluoromethoxy)phenyl | H | H | H | H | H | 247 |
| 68 | 2-methoxyphenyl | H | H | H | H | H | 205–207 |
| 69 | 3-chlorophenyl | H | H | H | H | H | >250 |
| 70 | 2-hydroxyphenyl | H | H | H | H | H | >250 |
| 71 | 4-methylphenyl | H | H | H | H | H | >250 |
| 72 | 3-methylphenyl | H | H | H | H | H | >250 |
| 73 | 2,4-dichlorophenyl | H | H | H | H | H | 235 |
| 74 | 3,5-dichlorophenyl | H | H | H | H | H | >250 |
| 75 | 3-methoxyphenyl | H | H | H | H | H | 191 |

-continued
| Example No. | R¹ | R² | R³ | R⁴ | R⁵ | R⁶ | Melting point °C. |
|---|---|---|---|---|---|---|---|
| 76 | 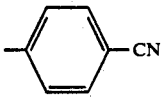 4-CN-phenyl | H | H | H | H | H | >250 |
| 77 | 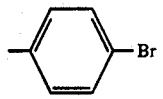 4-Br-phenyl | H | H | H | H | H | 264 |
| 78 | 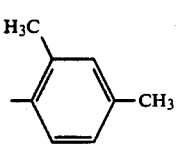 2,5-(CH₃)₂-phenyl | H | H | H | H | H | 188 |
| 79 | 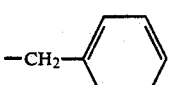 —CH₂-phenyl | H | H | H | —OCH₃ | —OCH₃ | >200 |
| 80 | 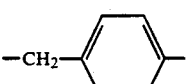 —CH₂-(4-Cl-phenyl) | H | H | H | —OCH₃ | —OCH₃ | >200 |
| 81 | 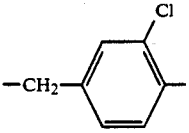 —CH₂-(3,4-diCl-phenyl) | H | H | H | —OCH₃ | —OCH₃ | >200 |
| 82 | 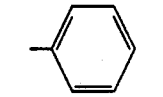 phenyl | CH₃ | H | H | H | H | >200 |
| 83 | 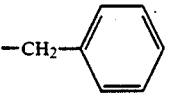 —CH₂-phenyl | CH₃ | H | H | H | H | Oil; ¹H-NMR*: 4,737 |
| 84 | C₂H₅ | C₂H₅ | H | H | H | H | 195 |
| 85 | 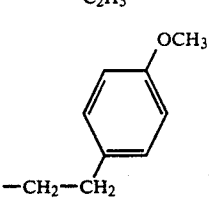 —CH₂—CH₂-(4-OCH₃-phenyl) | H | H | H | H | H | >200 |
| 86 | 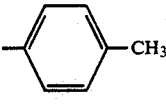 4-CH₃-phenyl | CH₃ | H | H | H | H | >200 |
| 87 | 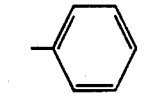 phenyl | C₂H₅ | H | H | H | H | >200 |
| 88 | 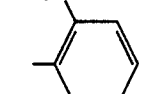 2-CH₃-phenyl | C₂H₅ | H | H | H | H | >200 |

-continued

| Example No. | R¹ | R² | R³ | R⁴ | R⁵ | R⁶ | Melting point °C. |
|---|---|---|---|---|---|---|---|
| 89 | cyclohexyl | CH₃ | H | H | H | H | >200 |
| 90 | phenyl | —(CH₂)₂—OH | H | H | H | H | >200 |
| 91 | CH₃ | —(CH₂)₂—CN | H | H | H | H | >200 |
| 92 | n-C₃H₇ | H | H | H | H | H | 154 |
| 93 | n-C₆H₁₃ | H | H | H | H | H | 93 |
| 94 | —(CH₂)₃—OCH₃ | H | H | H | H | H | Oil; ¹H-NMR*: 3,254 |
| 95 | 4-(CH₃CONH)-C₆H₄— | H | H | H | H | H | >250 |
| 96 | i-C₃H₇ | H | H | H | H | H | 172 |
| 97 | s-C₄H₉ | H | H | H | H | H | 101 |
| 98 | —CH₂-(2,4-Cl₂-C₆H₃) | CH₃ | H | Cl | H | H | >200 |
| 99 | —CH₂—CH₂Cl | H | H | H | H | H | 135 |
| 100 | —CH₂—CH=CH₂ | H | H | H | H | H | 153 |
| 101 | —CH(CH₃)—C₆H₅ | CH₃ | H | Cl | H | H | 165 |
| 102 | 4-(HCONH)-C₆H₄— | H | H | H | H | H | 166 |
| 103 | —CH₂—CH₂—O—CH₃ | H | H | H | H | H | 146–147 |
| 104 | 4-(H₂NCO)-C₆H₄— | H | H | H | H | H | >250 |
| 105 | 4-(CH₃OCO)-C₆H₄— | H | H | H | H | H | >250 |
| 106 | 4-(CH₃CO)-C₆H₄— | H | H | H | H | H | 250 |
| 107 | —CH₂—CH₂—OH | H | H | H | H | H | >200 |
| 108 | —CH₂—C≡CH | H | H | H | H | H | 176 |

-continued

| Example No. | R¹ | R² | R³ | R⁴ | R⁵ | R⁶ | Melting point °C. |
|---|---|---|---|---|---|---|---|
| 109 | -CH₂-(2,4-dichlorophenyl) | CH₃ | Cl | H | H | H | Oil |
| 110 | -(4-(N(CH₃)CHO)phenyl) | H | H | H | H | H | >200 |
| 111 | t-C₄H₉ | H | H | H | H | H | 145 |
| 112 | -CH₂-CN | H | H | H | H | H | >200 |
| 113 | i-C₄H₉ | H | H | H | H | H | 146 |
| 114 | -C(CH₃)₂-CH₂-CH₃ | H | H | H | H | H | 126 |
| 115 | C₂H₅ | H | H | H | H | H | 162 |
| 116 | -(CH₂)₃-C(O)-OCH₃ | H | H | H | H | H | 110 |
| 117 | n-C₁₈H₃₇ | H | H | H | H | H | 175 |
| 118 | -C(CH₃)₂-C≡CH | H | H | H | H | H | 172 |
| 119 | -CH(C₂H₅)-(4-methylphenyl) | H | H | H | H | H | 163 |
| 120 | -CH(CH₃)-(CH₂)₂-(3-chlorophenyl) | H | H | H | H | H | 153 |
| 121 | -CH(CH₃)-(CH₂)₂-(2-chlorophenyl) | H | H | H | H | H | 85-87 |
| 122 | -C(CH₃)₂-C≡C-phenyl | H | H | H | H | H | >250 |
| 123 | -C(CH₃)₂-(CH₂)₂-(4-chlorophenyl) | H | H | H | H | H | 146-148 |
| 124 | 4-methylcyclohexyl | H | H | H | H | H | 203-205 |

-continued

| Example No. | R¹ | R² | R³ | R⁴ | R⁵ | R⁶ | Melting point °C. |
|---|---|---|---|---|---|---|---|
| 125 | 2,4-dimethyl-3-ethylphenyl (H₃C, CH₃, H₅C₂) | H | H | H | H | H | 216–217 |
| 126 | 2,6-diisopropylphenyl | H | H | H | H | H | 232 |
| 127 | 2,4,6-trimethylphenyl | H | H | H | H | H | 198–200 |
| 128 | 2,6-diethylphenyl | H | H | H | H | H | 198 |
| 129 | 2,4-dimethylphenyl | H | H | H | H | H | 199–200 |
| 130 | 3,3,5-trimethylcyclohexyl | H | H | H | H | H | 185 |
| 131 | 2,4,6-trimethylphenyl | H | H | H | H | H | 197–198 |
| 132 | 2-isopropylphenyl | H | H | H | H | H | 143–145 |
| 133 | 4-tert-butylphenyl | H | H | H | H | H | 247–249 |

-continued

| Example No. | R¹ | R² | R³ | R⁴ | R⁵ | R⁶ | Melting point °C |
|---|---|---|---|---|---|---|---|
| 134 | 2,4,5-trimethylphenyl | H | H | H | H | H | 210–212 |
| 135 | 2,4-diethyl-5-methylphenyl | H | H | H | H | H | 192–194 |
| 136 | n-C₄H₉ | n-C₄H₉ | H | H | H | H | oil |
| 137 | H₉C₄-n-CH(C₂H₅)-CH₂- | H₉C₄-n-CH(C₂H₅)-CH₂- | H | H | H | H | oil |
| 138 | CH₃ | CH₃ | H | H | H | H | 164–166 |
| 139 | —CH₂—CH₂—CH₂—CH₂— | | H | H | H | H | 260–262 |
| 140 | —CH₂—CH₂—CH₂—CH₂—CH₂— | | H | H | H | H | 190–192 |
| 141 | CH₃ | n-C₁₈H₃₇ | H | H | H | H | 68 |
| 142 | —CH(COOC₂H₅)—CH₂—CH₂—CH₂—CH₂— | | H | H | H | H | 125–127 |
| 143 | —CH₂—CH(COOC₂H₅)—CH₂—CH₂—CH₂— | | H | H | H | H | 108–110 |
| 144 | —CH₂—CH(CH₃)—O—CH(CH₃)—CH₂— | | H | H | H | H | 145–148 |
| 145 | —CH₂—CH₂—O—CH₂—CH₂— | | H | H | H | H | 144 |
| 146 | —CH₂—CH₂—CH(COOC₂H₅)—CH₂—CH₂— | | H | H | H | H | oil $n_D^{20} = 1,5492$ |

*The ¹H NMR spectra were recorded in deuterochloroform (CDCl₃) or hexadeutero-dimethyl sulphoxide (DMSO-d₆) with tetramethylsilane (TMS) as the internal standard. The figures given are the chemical shift as δ value in ppm.

USE EXAMPLES

In the following Use Examples A and B, the compound listed below was employed as comparison substance;

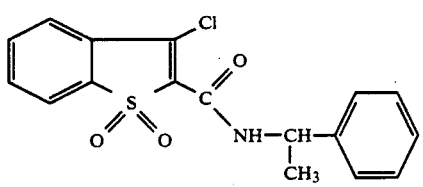

(A)

3-chloro-N-(1-phenylethyl)-benzothiophene-2-carboxamide S,S-dioxide (disclosed in DE-OS (German Published Specification) 3,832,848).

Example A

Ventura test (apple)/protective

Solvent: 4.7 parts by weight of acetone
Emulsifier: 0.3 parts by weight of alkyl-aryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dripping wet. After the spray coating has dried on, the plants are inoculated with an aqueous conidia suspension of the apple scab causative organism (*Venturia inaequalis*) and then remain in an incubation cabin at 20° C. and 100% relative atmospheric humidity for 1 day.

The plants are then placed in the greenhouse at 20° C. and a relative atmospheric humidity of about 70%.

Evaluation is carried out 12 days after the inoculation.

In this test, a clearly superior activity compared with the prior art is shown, for example, by the compounds of Preparation Examples: 1, 6, 16, 17, 23, 25, 29, 30.

Example B

*Leptosphaeria nodorum* test (wheat)/protective
Solvent: 100 parts by weight of dimethylformamide
Emulsifier: 0.25 parts by weight of alkyl-aryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dew-moist. After the spray coating has dried on, the plants are sprayed with a spore suspension of *Leptosphaeria nodorum*. The plants remain in an incubation cabin at 20° C. and 100% relative atmospheric humidity for 48 hours.

The plants are placed in a greenhouse at a temperature of approx. 15° C. and a relative atmospheric humidity of approx. 80%.

Evaluation is carried out 10 days after the inoculation.

In this test, a clearly superior activity compared with the prior art is shown, for example, by the compounds of Preparation Examples: 10, 28, 35, 36, 37.

Example C

Antimycotic in-vitro activity

Experimental set-up

The in-vitro tests were carried out using inocula of an average of $5 \times 10^3$ to $10^4$ microorganisms/ml of substrate. The following were used as nutrient media:
a) for dermatophytes and moulds: Sabouraud's "milieu d'epreuve"
b) for yeasts: meat extract/dextrose broth The incubation temperature was 28° C. to 37° C., the incubation time was 24 to 96 hours in the case of yeasts and 96 hours in the case of dermatophytes and moulds.

In this test, a good antimycotic activity is shown, for example, by the compounds according to the invention of Preparation Examples 1, 6, 9, 12, 15, 17, 24, 25, 27, 37, 41, 42, 43, 44, 46, 47, 49, 59, 62, 63, 64, 66, 78, 93, 111 and 114.

Example D

To demonstrate the activity against fungi or bacteria, the minimum inhibitory concentrations (MIC) of benzothiophene-2-carboxamide S,S-dioxides according to the invention were determined:

An agar which has been prepared from brewers' wort and peptone (fungi) or meat extract and peptone (bacteria) is treated with active compounds according to the invention at concentrations of 0.1 mg/l to 5000 mg/l. After the agar has solidified, it was contaminated with pure cultures of the test organisms listed in the Table. The MIC is determined after storage for 2 weeks at 28° C. and 60 to 70% relative atmospheric humidity. MIC is the lowest concentration of active compound at which no growth whatsoever by the microbe species used takes place; subjected to the tests were, for example, the Preparation Examples 93, 114, 113, 111, 92, 31, 41, 35 and 6.

The following compound was employed as comparison substance:

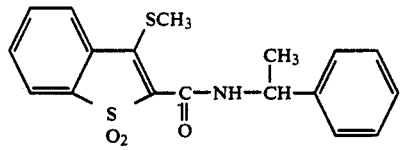

disclosed in DE 3,832,848.

Examples of test organisms: *Penicillium glaucum, Penicillium brevicaule, Chaetomium globosum, Aspergillus niger, Lentinus tigrinus, Sclerophoma pityophila, Trichoderma viride, Cladosporium herbarum, Alternaria tenuis, Aureobasidium pullulans, Staphylococcus aureus, Escherichia coli, Pseudomonas aeruginosa.*

I claim:

1. A benzothiophene-2-carboxamide S,S-dioxide of the formula (I)

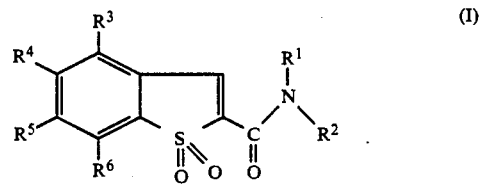

wherein
$R^1$ represents straight-chain or branched alkyl having 1 to 20 carbon atoms, or represents in each case straight-chain or branched halogenoalkyl, cyanoalkyl, hydroxyalkyl, alkoxyalkyl or alkoxycarbonylalkyl, each of which has 1 to 8 carbon atoms in the individual alkyl moieties, or represents straight-chain or branched alkenyl having 2 to 12 carbon atoms, or represents straight-chain or branched alkynyl having 2 to 12 carbon atoms, or represents cycloalkylalkyl or cycloalkyl, each of which has 3 to 7 carbon atoms in the cycloalkyl moiety and, in the case of cycloalkylalkyl, 1 to 6 carbon atoms in the straight-chain or branched alkyl moiety, and each of which is optionally monosubstituted to hexasubstituted in the cycloalkyl moiety by identical or different substituents, suitable cycloalkyl substituents in each case being: halogen, in each case straight-chain or branched alkyl having 1 to 4 carbon atoms or in each case straight-chain or branched halogenoalkyl having 1 to 4 carbon atoms and 1 to 9 identical or different halogen atoms; furthermore represents arylalkyl, arylalkenyl, arylalkynyl or aryl, each of which has 6 or 10 carbon atoms in the aryl moiety and, in the cases of arylalkyl, arylalkenyl and arylalkynyl, up to 12 carbon atoms in the respective straight-chain or branched alkyl or alkenyl or alkynyl moiety, each of which is optionally monosubstituted to pentasubstituted in the aryl moiety by identical or different substituents, suitable aryl substituents in each case being: halogen, cyano, nitro, formylamido, in each case straight-chain or branched alkyl, alkoxy or alkylthio, each of which has 1 to 4 carbon atoms, in each case straight-chain or branched halogenoalkyl, halogenoalkoxy, halogenoalkylthio, each of which has 1 to 4 carbon atoms and 1 to 9 identical or different halogen atoms, in each case straight-chain or branched alkylcarbonyl, alkoxycarbonyl, aminocarbonyl, N-alkylaminocarbonyl, N,N-dialkylaminocarbonyl, alkylcarbonylamino, N-alkyl-alkylcarbonylamino, N-alkyl-formylcarbonylamino or alkoximinoalkyl, each of which has 1 to 4 carbon atoms in the individual alkyl moieties, and phenyl which is optionally monosubstituted or polysubstituted by identical or different substituents from the group consisting of halogen and/or straight-chain or branched alkyl having 1 to 4 carbon atoms, $R^2$ represents hydrogen or straight-chain or branched alkyl which has 1 to 6 carbon atoms and which is optionally monosubstituted or polysubstituted by identical or different substituents, suitable substituents being: hydroxyl, halogen, cyano, and in each case straight-chain or branched alkoxy, alkoxycarbonyl or dialkylamino, each of which has 1 to 6 carbon atoms in the individual alkyl moieties, or $R^1$ and $R^2$ together with the nitrogen atom to which they are bonded represent a saturated 5- to 7-membered heterocycle which is optionally monosubstituted or polysubstituted by identical or different substituents and which can optionally contain 1 or 2 further hetero atoms selected from the group consisting of nitrogen, oxygen and sulphur, suitable substituents in in each case being: halogen, in each case straight-chain or branched alkyl, alkoxy or alkoxycarbonyl having in each case 1 to 4 carbon atoms or straight-chain or branched halogenoalkyl having 1 to 4 carbon atoms and 1 to 9 identical or different halogen atoms and $R^3$, $R^4$, $R^5$ and $R^6$ independently of one another in each case represent hydrogen, halogen, cyano, nitro or in each case straight-chain or branched alkyl, alkoxy, alkylthio, halogenoalkyl, halogenoalkoxy or halogenoalkylthio each of which has 1 to 6 carbon atoms and, in the case of halogenoalkyl, halogenoalkoxy or halogenoalkylthio, 1 to 13 identical or different halogen atoms.

2. A benzothiophene-2-carboxamide S,S-dioxide of the formula (I), according to claim 1, wherein $R^1$ represents straight-chain or branched alkyl having 1 to 18 carbon atoms, in each case straight-chain or branched halogenoalkyl, cyanoalkyl, hydroxyalkyl, alkoxyalkyl or alkoxycarbonylalkyl, each of which has 1 to 4 carbon atoms in the individual alkyl moieties, or represents straight-chain or branched alkenyl having 2 to 8 carbon atoms, or represents straight-chain or branched alkynyl 2 to 8 carbon atoms, or represents cycloalkylalkyl or cycloalkyl, each of which has 3 to 6 carbon atoms in the cycloalkyl moiety and, if appropriate, 1 to 4 carbon atoms in the straight-chain or branched alkyl moiety and each of which is optionally monosubstituted to tetrasubstituted in the cycloalkyl moiety by identical or different substituents, suitable cycloalkyl substituents in each case being: fluorine, chlorine, bromine, methyl, ethyl, n-or i-propyl, n-, i-, s- or t-butyl, chloromethyl, methyl, dichloromethyl or trifluoromethyl; moreover arylalkyl, arylalkenyl, arylalkynyl aryl, each of which has 6 or 10 carbon atoms in the aryl moiety and, in the cases of arylalkyl, arylalkenyl and arylalkynyl, up to 8 carbon atoms in the particular straight-chain or branched alkyl or alkenyl or alkynyl moiety and each of which is optionally monosubstituted to pentasubstituted in the aryl moiety by identical or different substituents, suitable aryl substituents in each case being: halogen, hydroxyl, cyano, nitro, formylamido, in each case straight-chain or branched alkyl, alkoxy or alkylthio, each of which has 1 to 4 carbon atoms, in each case straight-chain or branched halogenoalkyl, halogenoalkoxy, halogenoalkylthio, each of which has 1 to 4 carbon atoms and 1 to 9 identical or different halogen atoms, in each case straight-chain or branched alkylcarbonyl, alkoxycarbonyl, aminocarbonyl, N-alkylaminocarbonyl, N,N-dialkylaminocarbonyl, alkylcarbonylamino, N-alkyl-alkylcarbonylamino, N-alkyl-formylcarbonylamino or alkoximinoalkyl, each of which has 1 to 4 carbon atoms in the individual alkyl moieties, and phenyl which is optionally monosubstituted or polysubstituted by identical or different substituents from the group consisting of halogen and/or straight-chain or branched alkyl having 1 to 4 carbon atoms, $R^2$ represents hydrogen or alkyl which has 1 to 4 carbon atoms and which is optionally monosubstituted or polysubstituted by identical or different substituents, suitable substituents being: hydroxyl, halogen, cyano and in each case straight-chain or branched alkoxy, alkoxycarbonyl or dialkylamino, each of which has 1 to 4 carbon atoms in the individual alkyl moieties, or $R^1$ and $R^2$ together with the nitrogen atom to which they are bonded represent a heterocycle of the formula

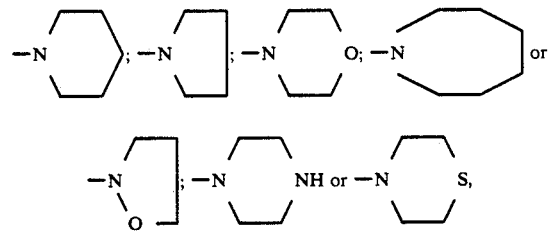

each of which is optionally monosubstituted to tetrasubstituted by identical or different substituents, suitable substituents in each case being: fluorine, chlorine, bromine, methyl, ethyl, n- or i-propyl, methoxy, ethoxy, methoxycarbonyl, ethoxycarbonyl, chloromethyl, trichloromethyl, dichloromethyl or trifluoromethyl, and $R^3$, $R^4$, $R^5$ and $R^6$ independently of one another in each case represent hydrogen, halogen, cyano, nitro or in each case straight-chain or branched alkyl, alkoxy, alkylthio, halogenoalkyl, halogenoalkoxy or halogenoalkylthio, each of which has 1 to 4 carbon atoms and, in the cases of halogenoalkyl, halogenoalkoxy or halogenoalkylthio, 1 to 9 identical or different halogen atoms.

3. A benzothiophene-2-carboxamide S,S-dioxide of the formula (I) according to claim 1, wherein $R^1$ represents methyl, ethyl, n- or i-propyl, n-, i-, s- or t-butyl, n- or i-pentyl, n- or i-hexyl, n- or i-heptyl, n- or i-octyl, n- or i-nonyl, n- or i-decyl, n- or i-dodecyl, n- or i-octadecyl, allyl, n- or i-butenyl, n- or i-pentenyl, n- or i-hexenyl, propargyl, n- or i-butinyl, n- or i-pentinyl, n- or i-hexinyl, chloromethyl, bromomethyl, chloroethyl, bromoethyl, chloropropyl, bromopropyl, cyanomethyl, cyanoethyl, cyanopropyl, hydroxymethyl, hydroxyethyl, hydroxypropyl, methoxymethyl, methoxyethyl, methoxypropyl, ethoxymethyl, ethoxyethyl, ethoxypropyl, methoxycarbonylmethyl, methoxycarbonylethyl, methoxycarbonylpropyl, ethoxycarbonylmethyl, ethoxycarbonylethyl, ethoxycarbonylpropyl, propoxycarbonylmethyl, propoxycarbonylethyl, propoxycarbonylpropyl; furthermore represents cyclopropyl, cyclopropylmethyl, cyclopropylethyl, cyclopropylpropyl, cyclopentyl, cyclopentylmethyl, cyclopentylethyl, cyclopentylpropyl, cyclohexyl, cyclohexylmethyl, cyclohexylethyl or cyclohexylpropyl, each of which is optionally monosubstituted to tetrasubstituted in the cycloalkyl moiety by identical or different substituents from the group consisting of fluorine, chlorine, bromine, methyl, ethyl, n-or i-propyl, chloromethyl, dichloromethyl or trifluoromethyl; furthermore represents phenylalkyl, phenylalkenyl, phenyl alkynyl, phenyl or naphthyl, each of which has, in the case of phenylalkyl, phenylalkenyl and phenylalkynyl, up to 6 carbon atoms in the straight-chain or branched alkyl or alkenyl or alkynyl moiety and each of which is optionally monosubstituted to trisubstituted in the aryl moiety by identical or different substituents, suitable aryl substituents in each case being: fluorine, chlorine, bromine, hydroxyl, cyano, nitro, methyl, ethyl, n- or i-propyl, n-, i-, s- or t-butyl, methoxy, ethoxy, n- or i-propoxy, n-, i-, s- or t-butoxy, methylthio, ethylthio, trifluoromethyl, trifluoromethoxy, trifluoromethylthio, methylcarbonyl, ethylcarbonyl, methoxycarbonyl, ethoxycarbonyl, aminocarbonyl, N-methylaminocarbonyl, N,N-dimethylaminocarbonyl, N-ethylaminocarbonyl, N,N-diethylaminocarbonyl, N-formylamino, N-acetylamino, N-methyl-N-formylamino, N-methyl-N-acetylamino, N-ethyl-N-formylamino, N-ethyl-N-acetylamino, methoximinomethyl, methoximinoethyl, ethoximinomethyl, ethoximinoethyl, or phenyl which is optionally monosubstituted to trisubstituted by identical or different substituents from the group consisting of fluorine, chlorine, bromine, methyl and/or ethyl, $R^2$ represents hydrogen, methyl, ethyl, n- or i-propyl, n-, i-, s- or t-butyl, n- or i-pentyl, n- or i-hexyl, hydroxymethyl, hydroxyethyl, hydroxypropyl, chloromethyl, bromomethyl, chloroethyl, bromoethyl, chloropropyl, bromopropyl, cyanomethyl, cyanoethyl, cyanopropyl, hydroxymethyl, hydroxyethyl, hydroxypropyl, methoxymethyl, methoxyethyl, methoxypropyl, ethoxymethyl, ethoxyethyl, ethoxypropyl, methoxycarbonylmethyl, methoxycarbonylethyl, methoxycarbonylpropyl, ethoxycarbonylmethyl, ethoxycarbonylethyl, ethoxycarbonylpropyl, propoxycarbonylmethyl, propoxycarbonylethyl, propoxycarbonylpropyl, dimethylaminomethyl, diethylaminomethyl, dipropylaminomethyl, dimethylaminoethyl, diethylaminoethyl, dipropylaminoethyl, dimethylaminopropyl, diethylaminopropyl ordipropylaminopropyl or $R^1$ and $R^2$ together with the nitrogen atom to which they are bonded represent a heterocycle of the formula

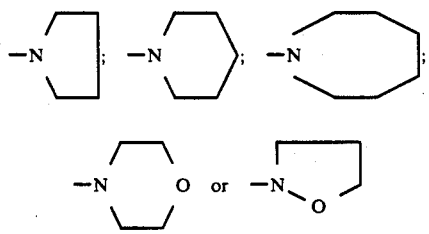

each of which is optionally monosubstituted, disubstituted or trisubstituted by methyl and/or ethyl and/or methoxycarbonyl and/or ethoxycarbonyl, $R^3$, $R^4$, $R^5$ and $R^6$ independently of one another in each case represent hydrogen, fluorine, chlorine, bromine, cyano, nitro, methyl, ethyl, n- or i-propyl, n-, i-, s- or t-butyl, methoxy, ethoxy n- or i-propoxy, n-, i-, s- or t-butoxy, methylthio, ethylthio, trifluoromethyl, trifluoromethoxy or trifluoromethylthio.

4. A microbiocidal composition comprising an effective amount of a compound according to claim 1.

5. A method of combating microorganisms which comprises applying to such microorganisms or to a pesticide habitat a microbiocidally effective amount of a compound according to claim 1.

6. A method of combating mycoses in the human and animal sector which comprises administering to said human or animal an antimycotically effective amount of a compound according to claim 1.

* * * * *

UNITED STATES PATENT AND TRADEMARK OFFICE
CERTIFICATE OF CORRECTION

PATENT NO. : 5,244,893
DATED : September 14, 1993
INVENTOR(S) : Elbe, et al.

It is certified that error appears in the above-indentified patent and that said Letters Patent is hereby corrected as shown below:

| | |
|---|---|
| Col. 41, line 62 | Delete " methyl " |
| Col. 44, line 13-14 | Delete " ordipropylaminopropyl " and substitute -- or dipropylaminopropyl-- |
| Col. 44, line 45 | Delete " pesticide " and substitute -- microbiocide -- |

Signed and Sealed this

Thirtieth Day of April, 1996

Attest:

BRUCE LEHMAN

*Attesting Officer*    Commissioner of Patents and Trademarks